United States Patent [19]

Nakagaki et al.

[11] Patent Number: 4,992,262

[45] Date of Patent: Feb. 12, 1991

[54] PROCESS FOR PRODUCING POWDER-BASED SOLID COSMETIC

[75] Inventors: Tomonari Nakagaki, Mitaka; Mamoru Ishii, Sagamihara; Haruo Ishibashi, Hatano, all of Japan

[73] Assignee: Asanuma Sogyo Kabushiki Kaisha, Tokyo, Japan

[21] Appl. No.: 501,978

[22] Filed: Mar. 29, 1990

Related U.S. Application Data

[63] Continuation of Ser. No. 122,634, Nov. 12, 1987, abandoned.

[30] Foreign Application Priority Data

May 17, 1984 [JP] Japan ................................ 59-99493

[51] Int. Cl.$^5$ ............................................. A61K 7/035
[52] U.S. Cl. ......................................... 424/63; 424/64; 424/65; 424/69; 424/DIG. 5
[58] Field of Search ....................... 424/63, 64, 65, 69, 424/DIG. 5

[56] References Cited

U.S. PATENT DOCUMENTS

| | | | |
|---|---|---|---|
| 3,800,034 | 3/1974 | Kircher et al. | 424/63 |
| 4,113,852 | 9/1978 | Kenkare et al. | 424/68 |
| 4,152,416 | 5/1979 | Spitzer et al. | 424/65 |
| 4,379,136 | 4/1983 | Mochida | 424/65 |
| 4,431,673 | 2/1984 | Goldner et al. | 424/DIG. 5 |

FOREIGN PATENT DOCUMENTS

| | | |
|---|---|---|
| 135060 | 3/1985 | European Pat. Off. . |
| 139481 | 5/1985 | European Pat. Off. . |
| 661524 | 7/1929 | France . |
| 118435 | 8/1918 | United Kingdom . |

*Primary Examiner*—Jacqueline Stone
*Attorney, Agent, or Firm*—Armstrong, Nikaido, Marmelstein, Kubovcik and Murray

[57] ABSTRACT

Method for producing powder-based solid cosmetic by mixing powdered cosmetic ingredients and organic bentonite with a volatile chlorofluorohydrocarbon-containing solvent and then shaping and drying the mixture. This method produces makeup cosmetics having no oily, sticky feeling and having excellent adhesiveness.

22 Claims, No Drawings

PROCESS FOR PRODUCING POWDER-BASED SOLID COSMETIC

This application is a continuation of application Ser. No. 122,634, filed Nov. 12, 1987, which is a continuation of application Ser. No. 734,354, filed May 14, 1985, both now abandoned.

BACKGROUND OF THE INVENTION

The present invention relates to a process for producing a powder-based solid cosmetic by solidifying powder particles with a binder, and a cosmetic product prepared by this process.

Conventional makeup cosmetics are prepared by mixing powdered cosmetic ingredients with fat or wax and shaping the resulting mixture. These conventional cosmetics are oily and sticky, and the makeup obtained upon application wears off rapidly. They also do not feel good to the makeup wearer, and do not have satisfactory adherence to the skin. Furthermore, these cosmetics containing fat or wax are formed by pressing the ingredients, or in the alternative, by heating the ingredients, handling them while they are in molten state to shape them, then cooling the obtained product. These steps are time-consuming and costly.

A process for producing a powder-based solid cosmetic has been proposed which consists of solidifying powdered cosmetic ingredients with a binder which is soluble in non-aqueous solvents such as methyl cellulose, rosin, shellac, wax, polyvinyl acetate, and acrylate polymer. This process, however, has a disadvantage in that the binder migrates in the drying step to form a film on the surface of the solid, and such film prevents the complete drying of the solid.

SUMMARY OF THE INVENTION

An object of the present invention is to obtain a powder-based solid cosmetic having adequate strength in its solid form, and giving a long-lasting makeup finish which has good adhesion to the skin, does not feel oily or sticky but feels good to the makeup wearer.

Another object of the present invention is to provide a process for producing a powder-based solid cosmetic which is easy to dry in the course of its manufacture.

DETAILED DESCRIPTION OF THE INVENTION

In the process for producing a powder-based solid cosmetic according to the present invention, the above-described objects are achieved by mixing a powdered cosmetic composition and organic bentonite with a volatile solvent which is a chlorofluorohydrocarbon or consists essentially of such chlorofluorohydrocarbon, then shaping the resulting mixture, and drying the shaped cosmetic item.

The formulation used in this process contains the following essential ingredients: a powdered cosmetic composition which consists essentially of powdered cosmetic ingredients; organic bentonite; and a volatile chlorofluoro-hydrocarbon-containing solvent. With this formulation, it is believed that, upon reaction with the solvent, organic bentonite swells to form a network structure which exhibits an effective binder function, absorbs the powdered cosmetic composition, and retains its shape even after the solvent has evaporated. Thus, the powder-based solid cosmetic of this invention has the proper strength, hardness, and breakage resistance in its solid form, and yet it feels good upon use, has good adherence to the skin, and gives good makeup durability.

In a conventional process for producing a powder-based solid cosmetic, a binder is used which is soluble in the non-aqueous solvent used. As a result, a film tends to form on the surface of the cosmetic product during the drying step in the course of the manufacturing process. This problem is not encountered in the process of this invention because the organic bentonite used is not soluble in the solvent used.

Furthermore, when a binder which is soluble in a non-aqueous solvent is mixed with powdered cosmetic ingredients which are water-repellent, there is a tendency for the inside of the cosmetic item to be difficult to fix. This problem is not encountered in the process of the present invention because the organic bentonite has good miscibility with the water-repellent powdered cosmetic ingredients.

The process of this invention has additional advantages in that the chlorofluorohydrocarbon-containing solvent used is safe for workers and does not present a fire hazard, thus it can be removed simply by drying.

The powdered cosmetic composition used in this invention consists essentially of powdered cosmetic ingredients. Examples of such powdered ingredients which are commonly used in makeup cosmetics are: white pigment such as titanium oxide, zinc oxide, zirconium oxide or the like; color pigment such as red iron oxide, yellow iron oxide, black iron oxide, ultramarine blue, Berlin blue, chromium oxide, chromium hydroxide, carbon black, coal tar coloring material, natural coloring matter or the like; pearlescent pigment such as fish scale guanine, mica titanium, bismuth oxychloride or the like; metallic soap such as magnesium stearate, calcium stearate, aluminum stearate, zinc laurate, zinc palmitate or the like; extender pigment such as talc, kaoline, white mica powder, magnesium carbonate, calcium carbonate, aluminum silicate, magnesium silicate, calcium silicate, clay, starch, nylon powder, polyethylene powder or the like; metallic pigment such as aluminum powder or the like.

It is known that cosmetics which are improved in feeling, adherence and spreadability can be prepared with the above-mentioned powdered cosmetic ingredients if they have been surface-treated with a silicone such as methyl hydrogen polysiloxane, with metallic soap, or with salts of N-acyl amino acids, in particular salts of N-acyl-L-glutamic acid. Such treatment imparts a cosmetically desirable water repellency to the powdered cosmetic ingredients. In the process of this invention, the powdered cosmetic ingredients used may be of the treated or untreated variety, or a mixture of both. They may be properly formulated according to the type of cosmetics and their intended usage.

The organic bentonite used in this invention is prepared from bentonite by reacting with cationic surface active agent to form the thickening and gelation of non-aqueous solvent, and one which is conventionally used to prevent the precipitation of pigment and pearl essence in nail enamel. In this invention, however, it is used as a binder for the powdered cosmetic composition. It is believed that the organic bentonite swells, without dissolving in a solvent, to form a network which absorbs the powdered cosmetic composition and retains its shape after the solvent has been removed.

The powder-based solid cosmetic which contains organic bentonite as a binder has desired physical properties such as strength, hardness, and flexural resistance in its solid form. Upon use, this cosmetic has the characteristic of feeling good to the makeup wearer for a prolonged period. These effects are not observed when inorganic bentonite or a hydrophilic binder is used.

The organic bentonite used in this invention is not particularly limited. Commercially available organic bentonite can be used. Preferred examples of commercial products include "Bentone" made by National Lead Industries, Inc. (U.S.), "S-ben" made by Hojun Yoko Co., and "Olben" made by Shiraishi Kogyo Co. They are equivalent to stearalkonium hectorite (Bentone 27), quarternium-18 bentonite (Bentone 34), and quarternium-18 hectorite (Bentone 38), respectively, which are listed in the Cosmetic Ingredients Dictionary issued by CTFA (The Cosmetic, Toiletry and Fragrance Association, Inc.).

The proportion of organic bentonite in the formulation is generally in the range from 0.05 wt% to 40 wt% based on the quantity of powdered cosmetic composition used. The preferred range is from 0.1 wt% to 15 wt% for producing a powder-based solid cosmetic which has good strength and organoleptic properties such as touch, feel, adherence, and makeup durability. If the proportion of organic bentonite is less than 0.05 wt%, shaping is difficult and the resulting product is poor in strength even if shaping is possible. Organic bentonite in excess of 40 wt% gives a product which is poor in feel and touch.

Organic bentonite may be used in combination with solvent-insoluble microcrystalline cellulose or metallic soap which increases the strength and helps to maintain the shape of the product.

The volatile solvent used in the process of this invention is a volatile chlorofluorohydrocarbon, or consists essentially of such chlorofluorohydrocarbon. The chlorofluorohydrocarbon causes the organic bentonite to swell completely, thereby allowing the organic bentonite to act as a binder.

The solvent used in the process of this invention is low-boiling, has low toxicity, and is non-flammable. Therefore, its removal from the shaped cosmetic product can be done simply by drying. No specially adapted precautions or equipment are required since the solvent does not present a health risk or a fire risk.

Suitable volatile chlorofluorohydrocarbons are 1,1,1- and 1,1,2-trichlorofluoroethane, with 1,1,2-trichlorofluoroethane being preferred. Commercially available solvents containing trichlorofluoroethane can be used. Examples of such commercially available volatile solvents include "Fronshowa" made by Showa Denko Co., "Freon" made by Mitsui Fluorochemical Co., "Fronsolve" made by Asahi Glass Co., and "CG Trifron" made by Central Glass Co., all being Japanese corporations. Table 1 shows the physical properties of some typical commercial solvents.

TABLE 1

| Product Name | Fronshowa FS-3 | CG Trifron A | Fronsolve AE |
|---|---|---|---|
| Molecular formula and composition | $CCl_2F-CClF_2$ | $\frac{\text{Acetone}}{CCl_2F-CClF_2} = \frac{12.5}{87.5}$ | $\frac{\text{Ethanol}}{CCl_2F-CClF_2} = \frac{4.0}{96.0}$ |
| Molecular weight | 187.38 | — | — |
| Boiling point | 47.57° C. | 43.9° C. | 44.7° C. |
| Flash point *1 | None | None | None |
| Toxicity *2 | 1000 ppm | ca. 1000 ppm | ca. 1000 ppm |

*1 The flashpoints (closed) of other solvents are as follows: Ethanol: 13° C., toluene: 4° C., trichloroethylene: none, and acetone: 18° C.
*2 The maximum tolerance established by ACGIH. Values for other solvents are as follows: Ethanol: 1000 ppm, toluene: 100 ppm and trichloroethylene: 100 ppm.
*The flashpoint and toxicity of other solvents are shown to illustrate the advantages of the solvents used in this invention, with respect to the safety and health of workers.

The amount of volatile solvent in the cosmetic formulation is preferably in the rang of 0.3 to 6 times (by weight) the total amount of the powdered cosmetic composition and organic bentonite. If this ratio is less than 0.3 times, the formulation does not solidify readily. If this ratio is greater than 6 times, the formulation takes an excessively long time to solidify and the solvent is lost.

In addition to the above-mentioned essential ingredients, i.e., powdered materials, organic bentonite, and volatile chlorofluorohydrocarbon-containing solvent, the cosmetic formulation used in the process of this invention may be incorporated with a small amount of a polar substance such as propylene carbonate, ethanol and acid which enhances the binder effect of the organic bentonite. In addition, the formulation may be further incorporated with antiseptics, antioxidants, and ultraviolet absorbers which are commonly used to prevent degradation of the cosmetic with time.

EXAMPLES

The process of this invention is described with reference to the following examples and comparative examples, in which "parts" means "parts by weight". It is to be understood that the invention is not limited to the described examples.

EXAMPLE 1

EYE SHADOW

| Mica titanium | 95 parts |
|---|---|
| Bentone 38 | 5 parts |
| Perfume | quantity suitable |
| Fronsolve AE | 400 parts |

EXAMPLE 2

EYE SHADOW

| Amino acid-treated titanium mica | 95 parts |
|---|---|
| Bentone 38 | 5 parts |
| Perfume | quantity suitable |
| Fronsolve AE | 400 parts |

EXAMPLE 3
ROUGE

| | |
|---|---|
| Silicone-treated mica | 22 parts |
| Silicone-treated titanium mica | 22 parts |
| Silicone-treated talc | 34 parts |
| Silicone-treated inorganic pigment | 8 parts |
| Silicone-treated color pigment | 2.7 parts |
| Zinc stearate | 10 parts |
| S-ben | 1.3 parts |
| Perfume | quantity suitable |
| Antiseptic | quantity suitable |
| CG Trifron A | 300 parts |

EXAMPLE 4
FOUNDATION

| | |
|---|---|
| Metallic soap-treated talc | 50 parts |
| Metallic soap-treated sericite | 10 parts |
| Metallic soap-treated mica | 20 parts |
| Silicone-treated titanium oxide | 6 parts |
| Silicone-treated red iron oxide | 2.3 parts |
| Zinc stearate | 10 parts |
| Bentone 27 | 1.7 parts |
| Fronshowa FS-3 | 500 parts |

The products in the above-mentioned four examples were produced as follows. First, the powdered materials and organic bentonite were thoroughly mixed. Then the proper amounts of perfume and antiseptic were added. Finally, the volatile chlorofluorohydrocarbon-containing solvent was added to make a uniform mixture. The mixture was shaped into a stick, 8 mm in diameter, by using a press molder, following by drying at 40° C. for solvent removal. Thus were obtained stick-shaped products.

COMPARATIVE EXAMPLE 1
COMPACT POWDER

| | |
|---|---|
| Mica | 50.0 parts |
| Talc | 2.0 parts |
| Titanium oxide | 15.0 parts |
| Red iron oxide | 20.4 parts |
| Lanolin | 3.0 parts |
| Isopropyl myristate | 5.5 parts |
| Surfactant | 3.7 parts |
| Antiseptic | 0.1 parts |
| Perfume | 0.3 parts |
| "Isoper H"* | 20.0 parts |

*A synthetic volatile solvent derived from a petroleum hydrocarbon, boiling point 171-193° C., available from Humble Oil and Refinery Co. (USA)

COMPARATIVE EXAMPLE 2
EYE SHADOW

| | |
|---|---|
| Mica | 59.3 parts |
| Pearl essence | 15.0 parts |
| Inorganic pigment | 15.0 parts |
| Lanolin | 4.5 parts |
| Squalane | 4.5 parts |
| Surfactant | 1.0 part |
| Antiseptic | 0.5 parts |
| Perfume | 0.2 parts |
| Isopropyl alcohol | 30.0 parts |

The above-mentioned two comparative examples represent known formulations wherein fat or wax is used in the place of organic bentonite, and a volatile solvent is used which is not a volatile chlorofluorohydrocarbon-containing solvent. The products in these comparative examples were prepared as follows. First, the ingredients were uniformly mixed, and the mixture was shaped into a stick, 8 mm in diameter, by using an extruder, followed by drying at 60° C. for 24 hours. Thus were obtained stick-shaped products.

The powder-based solid cosmetics obtained in the above examples and comparative examples were subjected to a flexural test, disintegration test, and organoleptic test. The results are shown in Table 2.

TABLE 2

| | Examples | | | | Comp. Examples | |
|---|---|---|---|---|---|---|
| | No. 1 | No. 2 | No. 3 | No. 4 | No. 1 | No. 2 |
| Flexural test (g) | 310 | 433 | 750 | 980 | 218 | 52 |
| Disintegration (g) | 433 | 1860 | >2000 | >2000 | 220 | 70 |
| Organoleptic test | | | | | | |
| Adherence | Fair | Good | Good | Good | Poor | Poor |
| Slip | Fair | Good | Good | Good | Good | Poor |
| Strength | Good | Good | Good | Good | Good | Break |

Flexural test: Measured with a rheometer, Model NRM-3002D, made by Fudo Kogyo K.K. (distance between the supports: 20 mm; temperature: 30° C.)
Disintegration test: Measured with the same rheometer as mentioned above. The sample stick, 8 mm in diameter, was cut into a 5 mm long piece, and the force required to crush the piece in the direction of the diameter was measured.

What is claimed is:

1. A process for producing a powder-based solid cosmetic comprising the steps of:
   mixing (a) a powdered cosmetic composition consisting essentially of powdered cosmetic ingredients with (b) organic bentonite and (c) a volatile solvent consisting essentially of a volatile chlorofluorohydrocarbon which is liquid at room temperature and under atmospheric pressure, wherein the amount of volatile solvent (c) is in the range of 0.3 to 6 times by weight the combined amounts of powdered cosmetic composition (a) and organic bentonite (b);
   (2) shaping the resulting mixture into the shape of a cosmetic; and
   (3) drying the shaped cosmetic so as to remove said volatile solvent, thereby obtaining said powder-based solid cosmetic.

2. A process as in claim 1 wherein the amount of organic bentonite is 0.05 to 40 wt% based on the amount of powdered cosmetic composition.

3. A process as in claim 1 wherein at least one powdered cosmetic ingredient has been surface-treated prior to said mixing to impart water repellency thereto.

4. A process as in claim 3 wherein the powdered cosmetic ingredient which has been surface-treated is selected from the group consisting of a pigment and an extender pigment.

5. A process as in claim 3 wherein the powdered cosmetic ingredient has been treated with silicone.

6. A process as in claim 1 wherein the powdered cosmetic composition comprises at least one powdered cosmetic ingredient which has been surface-treated prior to said mixing to impart water repellency thereto and at least one powdered cosmetic ingredient which has not been surface treated for water repellency.

7. A process as in claim 1 wherein at least one powdered cosmetic ingredient is a white pigment.

8. A process as in claim 1 wherein the chlorofluorohydrocarbon is selected from the group consisting of 1,1,2-trichlorofluoroethane and 1,1,1-trichlorofluoroethane.

9. A process as in claim 1 wherein the chlorofluorohydrocarbon is 1,1,2-trichlorofluoroethane.

10. A process as in claim 3 wherein the powdered cosmetic ingredient has been treated with metallic soap.

11. A process as in claim 3 wherein the powdered cosmetic ingredient has been treated with a salt of an N-acylamino acid.

12. A process as in claim 1 wherein at least one powdered cosmetic ingredient is a color pigment.

13. A process as in claim 1 wherein at least one powdered cosmetic ingredient is a pearlescent pigment.

14. A process as in claim 1 wherein at least one powdered cosmetic ingredient is metallic soap.

15. A process as in claim 1 wherein at least one powdered cosmetic ingredient is starch.

16. A process as in claim 1 wherein at least one powdered cosmetic is nylon powder.

17. A powder-based solid cosmetic produced by a process which comprises the steps of:
  (1) mixing (a) a powdered cosmetic composition consisting essentially of powdered cosmetic ingredients with (b) organic bentonite and (c) a volatile solvent consisting essentially of a volatile chlorofluorohydrocarbon which is liquid at room temperature and under atmospheric pressure, wherein the amount of volatile solvent (c) is in the range of 0.3 to 6 times by weight the combined amounts of powdered cosmetic composition (a) and organic bentonite (b);
  (2) shaping the resulting mixture into the shape of a cosmetic; and
  (3) drying the shaped cosmetic so a to remove said volatile solvent, thereby obtaining said powder-based solid cosmetic;
  wherein at least one powdered cosmetic ingredient as been surface-treated prior to said mixing to impart water-repellency thereto, said treated powdered cosmetic ingredient being selected from the group consisting of a pigment and an extender pigment.

18. A powder-based solid cosmetic as in claim 17 wherein the amount of organic bentonite is 0.05 to 40 wt% based on the amount of powdered cosmetic composition.

19. A process for producing a powder-based solid cosmetic comprising the steps of:
  (1) mixing (a) a powdered cosmetic composition consisting essentially of powdered cosmetic ingredients with (b) organic bentonite, (c) a volatile solvent consisting essentially of a volatile chlorofluorohydrocarbon which is liquid at room temperature and under atmospheric pressure, and (d) a polar substance selected from the group consisting of propylene carbonate, ethanol, acetone and acids, wherein the amount of volatile solvent (c) is in the range of 0.3 to 6 times by weight the combined amounts of powdered cosmetic composition (a) and organic bentonite (b), and wherein the amount of the polar substance (d) is at most 14 wt% of the amount of the volatile solvent (c);
  (2) shaping the resulting mixture into the shape of a cosmetic; and
  (3) drying the shaped cosmetic so as to remove said volatile solvent, thereby obtaining said powder-based solid cosmetic.

20. A process as in claim 19 wherein the amount of organic bentonite is 0.05 to 40 wt% based on the amount of powdered cosmetic composition.

21. A powder-based solid cosmetic produced by a process which comprises the steps of:
  (1) mixing (a) a powdered cosmetic composition consisting essentially of powdered cosmetic ingredients with (b) organic bentonite, (c) a volatile solvent consisting essentially of a volatile chlorofluorohydrocarbon which is liquid at room temperature and under atmospheric pressure, and (d) a polar substance selected from the group consisting of propylene carbonate, ethanol, acetone and acids, wherein the amount of volatile solvent (c) is in the range of 0.3 to 6 times by weight the combined amounts of powdered cosmetic composition (a) and organic bentonite (b), and wherein the amount of the polar substance (d) is at most 14 wt% of the amount of the volatile solvent (c);
  (2) shaping the resulting mixture into the shape of a cosmetic; and
  (3) drying the shaped cosmetic so as to remove said volatile solvent, thereby obtaining said powder-based solid cosmetic;
  wherein at least one powdered cosmetic ingredient has been surface-treated prior to said mixing to impart water-repellency thereto, said treated powdered cosmetic ingredient being selected from the group consisting of a pigment and an extender pigment.

22. A powder-based solid cosmetic as in claim 21 wherein the amount of organic bentonite is 0.05 to 40 wt% based on the amount of powdered cosmetic composition.

* * * * *

UNITED STATES PATENT AND TRADEMARK OFFICE
CERTIFICATE OF CORRECTION

PATENT NO. : 4,992,262

DATED : February 12, 1991

INVENTOR(S) : Tomonari NAKAGAKI etal

It is certified that error appears in the above-identified patent and that said Letters Patent is hereby corrected as shown below:

On the title page, Item [63], insert, second line, after "doned.", -- Continuation of Ser. No. 734,354, May 14, 1985, abandoned. --

Signed and Sealed this

Eleventh Day of August, 1992

Attest:

DOUGLAS B. COMER

*Attesting Officer*  *Acting Commissioner of Patents and Trademarks*